United States Patent [19]
Valentino et al.

[11] Patent Number: 5,742,056
[45] Date of Patent: Apr. 21, 1998

[54] REAL TIME PET IMAGING PROCESSOR FOR A SINGLE PHOTON GAMMA CAMERA

[75] Inventors: Frank C. Valentino, Solon; Robert Zahn, Chagrin Falls; Frank P. DiFilippo, Mayfield Heights, all of Ohio

[73] Assignee: Picker International, Inc., Cleveland, Ohio

[21] Appl. No.: 752,559

[22] Filed: Nov. 21, 1996

Related U.S. Application Data

[60] Provisional application No. 60/007,512 Nov. 22, 1995.
[51] Int. Cl.⁶ .................................................. G01T 1/164
[52] U.S. Cl. .............................. 250/363.03; 250/363.04; 250/369
[58] Field of Search ........................ 250/363.03, 363.04, 250/363.02, 366, 369

[56] References Cited

U.S. PATENT DOCUMENTS

| | | | |
|---|---|---|---|
| 4,618,772 | 10/1986 | Haas et al. | 250/363.03 |
| 4,755,680 | 7/1988 | Logan | 250/263.03 |
| 4,980,552 | 12/1990 | Cho et al. | 250/363.03 |
| 5,331,553 | 7/1994 | Muehllehner et al. | |
| 5,457,321 | 10/1995 | Uchihara et al. | 250/363.04 |

*Primary Examiner*—Don Wong
*Attorney, Agent, or Firm*—Renner, Otto, Boisselle & Sklar, P.L.L.

[57] ABSTRACT

This invention addresses the practical implementation of PET imaging capability on a conventional gamma camera. The primary subject of this invention is the addition of a real time processor to perform the rebinning calculations and other on-the-fly calculations and procedures to make PET imaging on a gamma camera more practical. The rebinning or transformation operation described above is performed on-the-fly as each event pair is detected with an event throughput rate sufficient for clinical applications. This transformation process is performed by a chain of digital signal processing subsystems (or similar real time processors), with the resultant transformed data stored in a memory subsystem until a sufficient number of events have been received to produce an image of acceptable quality.

13 Claims, 4 Drawing Sheets

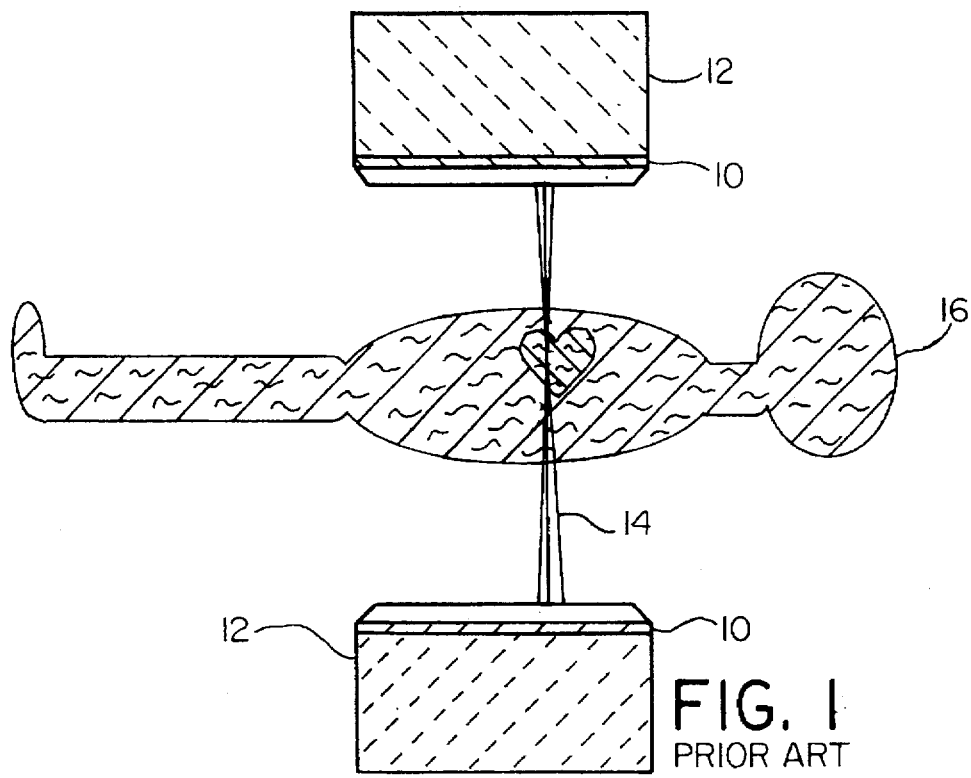
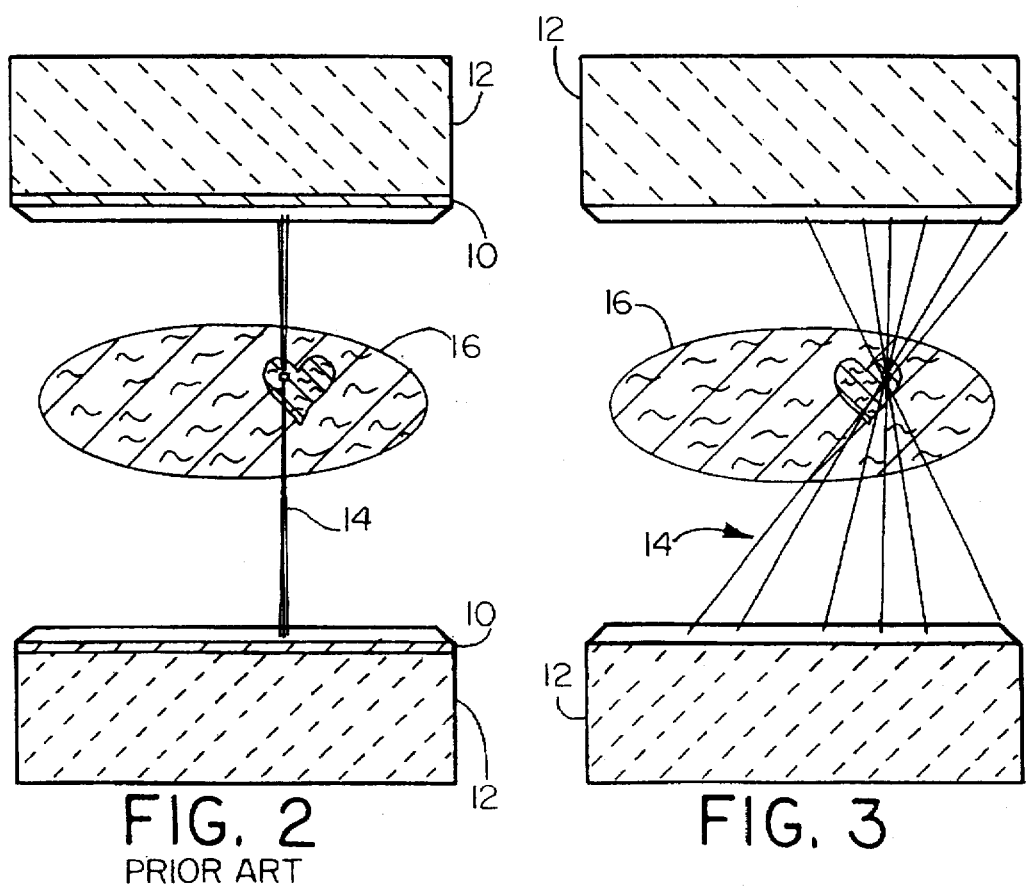
FIG. 1 PRIOR ART
FIG. 2 PRIOR ART
FIG. 3

REAL TIME PET IMAGING PROCESSOR FOR A SINGLE PHOTON GAMMA CAMERA

This application claims the benefit of U.S. Provisional Application No. 60/007,512, filed Nov. 22, 1995.

FIELD OF THE INVENTION

The invention described below relates generally to emission tomography, and more particularly, to a real time processor and method for providing improved emission tomography images.

BACKGROUND OF THE INVENTION

The demand for PET (Positron Emission Tomography) has been steadily increasing. However, the potential of the PET imaging market cannot be fully realized because the PET imaging agents in use today are very short lived and are generally cyclotron produced (this makes distribution very difficult and expensive), and because PET imaging systems are very expensive, ranging from $1.2 to $2.9 million each.

In positron emission tomography (PET) a radionuclide is administered internally to a living subject. A positron from the decaying radionuclide encounters and annihilates an electron resulting in a pair of annihilation photons (or gamma rays) which are emitted in nearly opposite (180°) directions from the annihilation site, each with an energy of 511 keV. Scintillation detectors are used to detect the emitted photons. A typical PET imaging system includes a ring of fixed scintillation detectors which completely surrounds the patient. Data acquisition software records events and determines whether any pair of events represent the gamma rays from the annihilation of a positron. This is done in part through a process called coincidence detection in which any pair of gamma rays with the proper energy that arrive at the detector ring simultaneously are considered to represent gamma rays resulting from the annihilation of a positron.

Today, there is an installed base of single photon emission computed tomography (SPECT) cameras in excess of 5000 units in the U.S. These SPECT cameras image a wide range of pharmaceuticals for diagnosis of an even greater range of disease. In SPECT, the photons detected are generated directly by the radionuclide rather than by the annihilation of a positron. The directly emitted photons do not come in pairs and generally have lower energies than do those resulting from positron annihilation. The cost of SPECT cameras ranges from $200,000 to $550,000. SPECT cameras have been built with one, two or three detectors mounted on a gantry so that the detectors can move around the patient.

For years, people have considered creating images on these widely available SPECT cameras from the gamma rays which result from the annihilation of positrons from a positron emitting pharmaceutical such as FDG. One way to do so on a standard SPECT camera has been to mount a lead collimator 10 in front of the detector 12 as illustrated in FIGS. 1 and 2. The collimator assures that the only photons with a desired trajectory reach the detector. Typically the photons with trajectories 14 that are perpendicular (or nearly perpendicular) to the detector surface are the ones which pass through the collimator to the detector surface in which case the collimator has holes that are parallel to each other and perpendicular to the detector surface. Other geometries for the collimator have also been used in which the collimator accepts a cone shaped beam or a fan shaped beam of photons. The type of collimator used can affect operating characteristics such as the sensitivity and resolution of the camera, and it affects the algorithms necessary to recreate the image from the collected data.

As each event is detected, its X and Y coordinates point to a location in a computer memory and the content of the memory at that location is incremented. This array of memory locations is referred to as a projection. Through tomography, each projection collected over the 360° surrounding the patient 16 is used to recreate the radioactive distribution within the patient. The geometry is relatively simple because the angle of incidence for each gamma ray is known to be nearly perpendicular to the face of the scintillation crystal.

In using a SPECT camera for PET imaging the lead collimator has been necessary because these systems were not designed for coincidence detection. Because a gamma ray emitted as a result of a positron emission has 511 keV in energy, the collimators must have very thick septa. This has resulted in very poor image resolution. In addition such a lead collimator is a very heavy assembly. Many SPECT cameras could not support this weight. However, as poor as the resolution was compared to PET systems, positron imaging using a SPECT camera was and still is very appealing to many users because of the low cost (under $20,000) to add a collimator to an already available SPECT camera.

There is a large installed base of large field of view multiple head SPECT cameras and a market for more of such cameras. The possibility of using these cameras for performing coincidence detection of the gamma rays resulting from positron annihilation has been appealing for a couple of reasons. First, the detectors oppose one another (in the case of dual head cameras or are at other known relative positions in the case of three headed cameras) making the geometry efficient for coincidence detection, and second, with coincidence detection, "electronic collimation" allows for the removal of the resolution degrading lead collimator.

Accordingly, in another approach to PET imaging using a SPECT camera the lead collimator has been removed, and so gamma rays can strike the detector at a range of angles. Coincidence circuitry has been used to determine if two gamma ray events occurred at the same time at each detector, indicating that the two events represent a positron emission and decay into two opposite gamma rays. In this case, without the collimator, event pairs can happen over a large range of angles (illustrated in FIG. 3) where in SPECT it is restricted to only those at about 0°. For purposes of discussion, the angle of incidence of a gamma ray with a detector may be broken into two components, one viewed in a plane perpendicular to the axis of the camera shown in FIGS. 3 and 4, called the transverse plane angle of incidence, and one viewed in a plane that includes the axis of the camera called the axial angle of incidence.

In PET applications the X and Y coordinates of an event on a single detector alone are no longer sufficient to point to a unique location in the projection acquisition matrix. This is true because the angle of incidence cannot be known from that information alone. However, the coordinates of coincident events on each detector ($X_{DET1}$, $Y_{DET1}$; $X_{DET2}$, $Y_{DET2}$) can be used along with the distance between detectors 20, 22 to determine the angle of incidence. See FIGS. 4 and 5. To construct a tomograph from this data the first step has been to transform the positions to a new frame of reference (herein termed the "index" frame of reference) in which the transverse plane angle of incidence is 90°. In FIG. 4 the position of the detectors 20 and 22 are assumed to be at 0° and 180°, respectively when the rays 26 hit the detectors. In the index frame of reference, the detectors are rotated clockwise to 36° and 216°, respectively, as shown in phantom in FIG. 4. The actual angle of incidence in the transverse plane (which measured about 56°) is shown to be 90° in the index frame of reference. The newly calculated $X_{index}$ and $Y_{index}$ (see FIGS. 4 and 6) have been used to index into projection frames exactly as in the SPECT case. This process is called rebinning. Once data is rebinned into projection frames, tomography can be done.

This rebinning process works well. However, existing SPECT camera systems do not have the capability to make this calculation directly. This is primarily because in multi-detector systems the detectors have independent processing channels. They do not know about one another and cannot compare data as it arrives. To overcome this the data has been collected in list mode, a fairly standard feature in most systems. In a list mode acquisition, the X, Y, E (energy) and detector acquisition angle signals from each detector are captured in a "list" format into memory. After data collection, through a software post process, the rebinning calculations are performed on an event-by-event basis creating the projection frames. The list mode is flexible since it allows the parameters for rebinning to be changed after the fact. For example the angle of incidence of a gamma ray can be used to determine whether or not the data will be used to form the image. Allowing a wide angle of acceptance increases sensitivity while decreasing resolution. With post processing from a list of data, both a high resolution image and a high sensitivity image can be created. However the list method has two major drawbacks. First, the memory and disk space requirements are very high. And second, because this rebinning process is done in software, it is slow (10-30 minutes).

SUMMARY OF THE INVENTION

The present invention provides a real time processor that can be added to a SPECT camera to allow practical (in terms of time and expense) PET data acquisition and processing. Users can operate the system in a way already familiar to them. The addition of this capability does not alter the operation of the current SPECT or planar operation. The real time processor of the present invention provides the following advantages: event validity is tested early to insure that an event pair is complete and in coincidence before performing further calculations; event discrimination (energy windowing) is performed quickly; a two dimensional or three dimensional angular or coordinate determination can be made quickly and easily; event framing (or rebinning) is performed more quickly; multiple rebinnings can be made based on user preferences (i.e., high sensitivity, low resolution at the same time as a low sensitivity, high resolution image where the axial angle of incidence is the determining rebinning factor); center of rotation and detector overlap compensation; whole body scanning provision; on-the-fly sensitivity correction due to geometry; and intrinsic detector corrections such as energy, linearity and uniformity may be incorporated in this processor.

One aspect of the present invention is a method of processing positron emission data collected from a gamma camera having an axis and a pair of detectors movable about a circular path in a plane transverse to the axis of the camera. The method includes the following steps. First, collecting data relating to the actual location including the actual angle of incidence and energy of events at each of two detectors and data relating to the angular position of the detector in its path at the moment of the events. Second, comparing the time of each event at each of the two detectors to determine whether the two events occurred simultaneously and rejecting the data if the events did not occur simultaneously. Next a correction factor may be applied to the energy data based on the geometry of the detector, and the corrected energy values may be compared to a range of acceptable values and rejecting the data if the corrected energy value is outside a selected range. Finally, the actual location data and actual angle of incidence data are transformed to an equivalent index location data for a perpendicular angle of incidence in the transverse plane at an equivalent index detector angular position, and thereafter recording an event by incrementing a tally at a memory location corresponding to the index location data and index detector angular position.

Another aspect of the present invention is the foregoing and includes recording events at memory locations corresponding to selected ranges of angular position in a plane which contains the axis of the camera.

The foregoing and other features of the invention are hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

FIG. 1 is a schematic side elevation view of a prior art SPECT gamma camera showing a patient between a pair of detectors each of which is equipped with a collimator and showing the gamma rays in one vertical plane from a radionuclide;

FIG. 2 is a view looking in the direction of arrow 2—2 in FIG. 1 imaging system.

FIG. 3 is a view similar to FIG. 2, but showing the detectors without collimators and arranged for PET imaging, and further illustrating the gamma rays in one plane transverse to the axis of the camera;

DETAILED DESCRIPTION OF THE INVENTION

The present invention provides a real time processor to perform the rebinning calculations and other on-the-fly calculations and procedures to make PET imaging on a gamma camera more practical. Practical real time PET coincidence imaging on a multiple detector SPECT gamma camera involves detecting two individual nuclear events within a pre-determined time window, one from each detector, and transforming the received data into a format that allows standard SPECT image reconstruction.

The rebinning or transformation operation described above is performed on-the-fly as each event pair is detected with an event throughput rate sufficient for clinical applications. This transformation process is performed by a chain of Digital Signal Processing Subsystems (or similar real time processors), with the resultant transformed data stored in a memory subsystem until a sufficient number of events has been received to produce an image of acceptable quality. After the data acquisition is complete, the prepared frame data (or projections) are transferred to a general purpose computer where the image reconstruction operation is performed in the same manner as in conventional SPECT processing. This combination of steps greatly reduces processing time to create an image as compared to the list method available heretofore.

Figure 7:
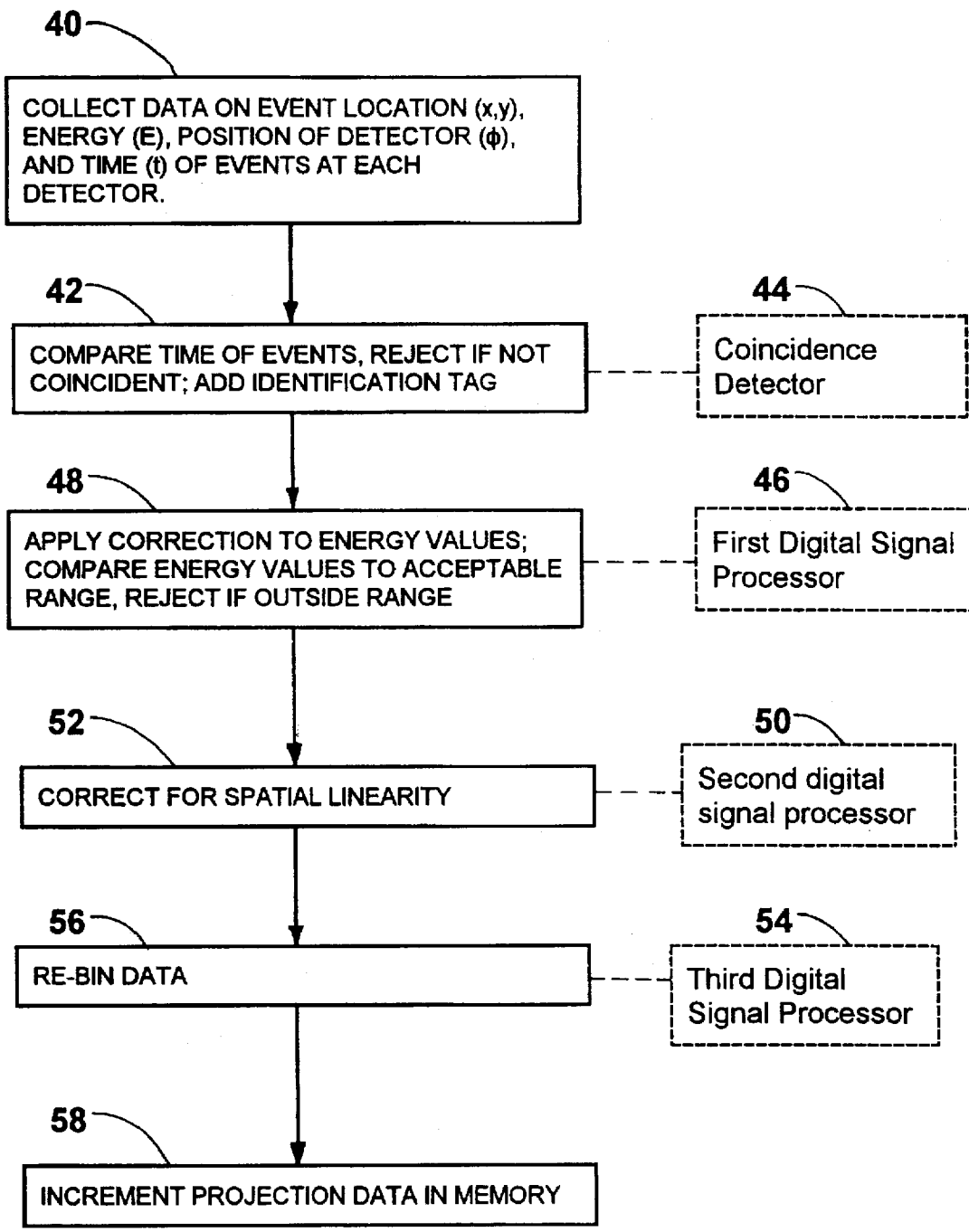
FIG. 7 is a block diagram showing the sequence of steps used in practicing the present invention.

FIG. 7 is a block diagram illustrating the various steps in the process of the present invention. These steps may be carried out by a hard wired system, in software or in a combination of the two. The following disclosure is intended to be sufficient to enable a software engineer or a circuit board designer familiar with nuclear imaging and the hardware and software used for nuclear imaging to practice the present invention.

As shown in block 40, event data is received from each detector. This data includes two values, X and Y, representing the location on the detector where the event occurred, as well as a value representing the energy, E, of the event. Each detector sends a conventional signal whenever an event occurs. These signals are compared at block 42 to determine whether the events at two detectors are "simultaneous". In practice, this is performed by a coincidence detector 44, where events are considered "simultaneous" if they occur within 15 nanoseconds of each other. Each event of a simultaneous event pair is then assigned an event identification tag which is the same for each event of the pair. Another component of the system (the rebinning processor) records the actual position of the detector in its gantry for each such event pair.

The addition of an identification tag is useful in order to accommodate the differences in response of the hardware processing the data from the two detectors. This is especially true where the invention is used in a SPECT gamma camera with a pair of detectors that were initially designed to operate independently of each other.

In the first Digital Signal Processor (DSP) 46 the identification tags of an event pair are compared, and if not identical, the pair is rejected as not being the result of a positron annihilation. If the timing tags match, the first DSP may perform an energy correction as shown at block 48. It is well known that the energy response of a detector can vary from place to place on the face of the detector, and similarly it is known to correct for this nonlinearity by using correction factors derived during calibration of the detector. The first DSP 46 the compares the corrected energy values for each event of the event pair to a predetermined range of energy values considered to be normal for the radionuclide in use. If the corrected energy value for either event of an event pair is outside the selected range (or ranges), then the pair is discarded. If the corrected energy values are within the selected acceptable range, then the event pair is passed to the second DSP 50, and the first DSP 46 is free to process the next coincident pair.

As shown at block 52 the second DSP 50 accepts the event pair data from the first DSP 46 and applies linearity corrections to the X and Y values. Such spatial linearity corrections are common in the prior art and are performed in a conventional manner based on correction factors determined during calibration of the camera. The corrected X, Y, and E values together with the identification tag are then passed to a third DSP 54, leaving the second DSP free to process data relating to the next coincident pair.

The third DSP 54 performs a rebinning operation shown schematically at block 56. This operation transforms the X, Y, and angular gantry position values of each event pair from their measured values to new, equivalent values in a different frame of reference. In this new frame of reference the detector is viewed along the axis of the machine and the detector is assumed to be in the angular position around the gantry where the incident gamma ray appears perpendicular to the face of the detector (again as viewed along the axis of the machine). This frame of reference is useful because from this frame of reference, termed the index frame of reference, the plane of the detector corresponds to the projection plane of a corresponding SPECT gamma camera, and once the rebinning is complete, the tomograph can be created in much the same manner as a conventional SPECT tomograph is created from its projections.

Figure 4:
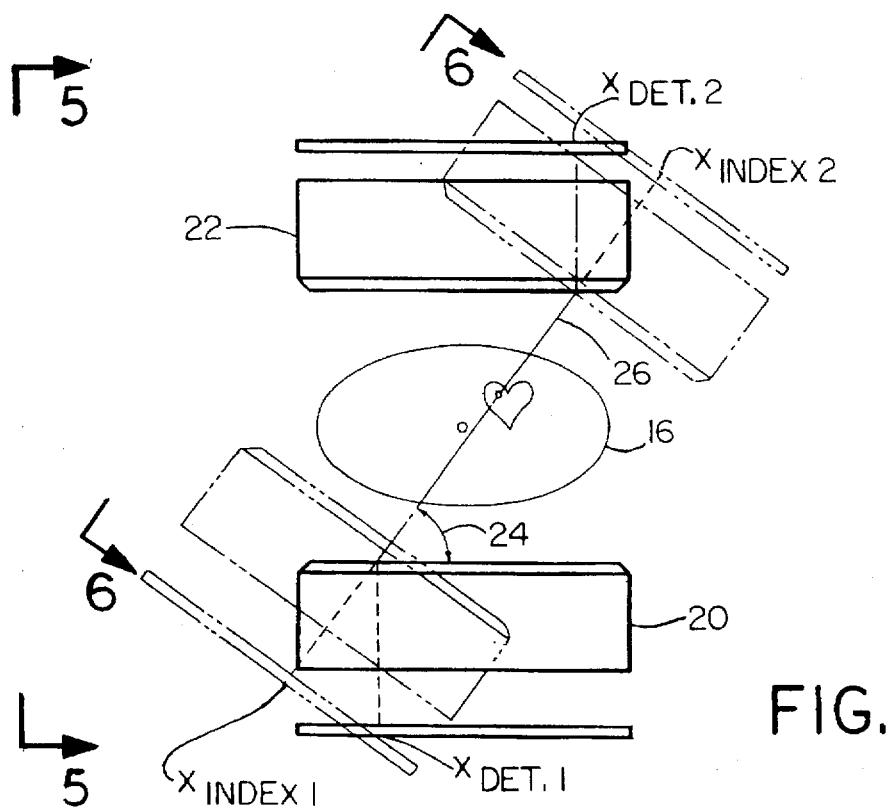
FIG. 4 is similar to FIG. 3, but illustrating a single, coincident pair of gamma rays and the transformation of the coordinates of the actual position of incidence of one of the rays and the position of the detector when the events occurred to the coordinates of the point where the ray would have struck the detector had the transverse angle of incidence of the ray been 90° and the corresponding position of the detector.
Figure 5:
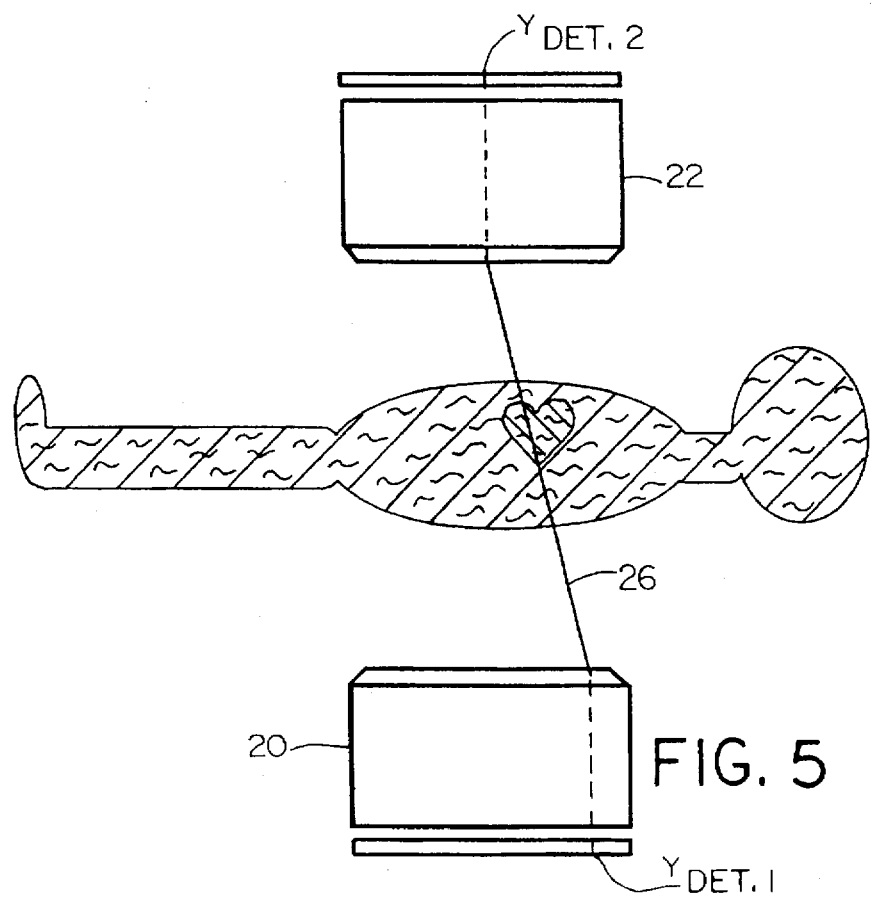
FIG. 5 is a view looking in the direction of arrows 5—5 in FIG. 4.

While the index frame of reference is conveniently selected to be the one where the incident gamma ray has a path perpendicular or within a few degrees of perpendicular to the plane of the detector as viewed in FIG. 4, this is not necessary. As with collimators that accept gamma rays that are not perpendicular, the angle of incidence in the transverse plane is selectable for various imaging purposes and need not be perpendicular. In the event that a non perpendicular transverse plane angle of incidence is desires, the third DSP 54 contains either an algorithm or a look up table which specifies the acceptable angles of incidence as a function of $X_{INDEX}$, $Y_{INDEX}$, just as in the fan beam or cone beam collimators the angle of the hole through the collimator varies across the face of the detector.

Figure 6:
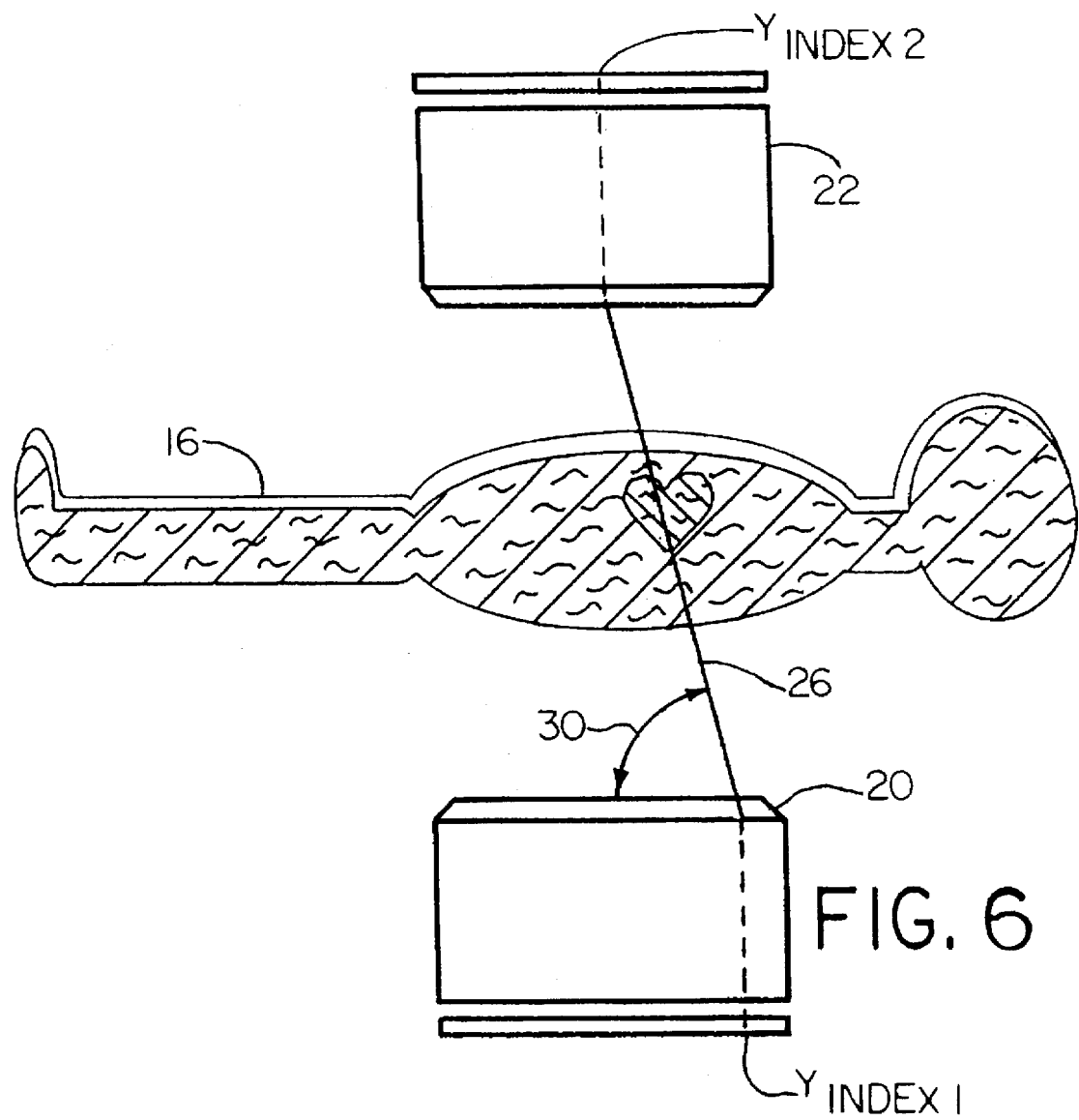
FIG. 6 is a view looking in the direction of arrows 6—6 in FIG. 4.

In the rebinning operation the X, Y and detector/gantry position values of an event pair are used to calculate new values $X_{INDEX}$, $Y_{INDEX}$ and angular index values for each event of an event pair. The $X_{INDEX}$ and $Y_{INDEX}$ values for each event represent the location on a detector where the event would have occurred if the detector had been in the position around the gantry where the ray would have struck the detector perpendicular to the face of the detector as viewed in a plane perpendicular to the axis of the machine. (This position of the detector is referred to as the "index position" and is illustrated in FIGS. 4 and 6.) The $X_{INDEX}$ and $Y_{INDEX}$ values for each detector (together with geometric information about the relative positions of the detectors with respect to one another) define a line in space which passes through the point where the positron was annihilated. The orientation of this line in space can also be defined by two angles, one of which is the angle of the detector's index position with respect to the gantry for this event pair. (In FIG. 4 the index position of the gantry and detector 21 is 36°) The other angle, termed the axial angle (shown at 30 in FIG. 6), is the angle the line makes with the detector face when the detector is in the index position and when viewed in a plane perpendicular to the face of the detector that includes the axis of the machine. The axial angle can be readily calculated from the $X_{INDEX}$ and $Y_{INDEX}$ values and geometric information about the relative positions of the detectors with respect to each other. Thus for each event pair, the rebinning operation calculates $X_{INDEX}$ and $Y_{INDEX}$ values, an axial angle value, and an index position value which reflects the detector head index position.

Once the rebinning calculation is complete, the data associated with an event pair is stored in a memory location (projection) associated with the particular detector head index position shown schematically in FIG. 7 at block 58. The data in each projection includes $X_{INDEX}$, $Y_{INDEX}$, and the axial angular index value. This data is stored until each projection has enough data that a tomograph can be reconstructed. The tomographic reconstruction can proceed using the axial angle as a filter, allowing a large angle of acceptance will produce a tomograph with relatively higher sensitivity but lower resolution. Alternatively, the tomographic reconstruction could be performed accepting only event pairs where the axial angular value is close to 90°, with the resulting tomograph having a high resolution but low sensitivity.

Other parameters may be selected for filtering the image produced. For example, the user may select an energy window, accepting only photons with energies at the photo peak, or accepting also photons with lower energies that result from Compton scattering or a further separation utilizing a cardiac gate. Because the rebinning process is done on the fly, the present invention allows multiple filters to be used simultaneously, so that images with various energy windows, various angles of acceptance, various stages of an organ's cycle can be specified at the beginning of the imaging process and then produced simultaneously.

It is anticipated that this real time processor can be extended to three dimensional reconstruction processes as well. The rebinning criteria may change depending on the algorithm selected and the real time processor would be reprogrammed as required. The rebinning algorithms used for the rebinning processes are similar to those used in the prior art devices which use the list method, with the difference being that the present invention applies the algorithms on the fly, that is as the data is collected, rather than after the fact.

Although the invention has been shown and described with respect to an exemplary embodiment thereof, it is obvious that equivalent alterations and modifications will occur to others skilled in the art upon the reading and understanding of the specification. The present invention includes all such equivalent alterations and modifications, and is limited only by the scope of the following claims.

What is claimed is:

1. A method of forming an image from positron emissions comprising the steps of:

collecting positron emission data from a gamma camera having an axis and a plurality of detectors with faces movable about a path in a plane transverse to the axis of the camera, the data relating to the actual location and energy of events at each of two of the detectors and to the actual angular position of each detector in its path at the moment of the events;

in a first real time processor comparing the time of each event at each of two detectors to determine whether the two events occurred simultaneously;

thereafter passing actual location data and actual energy data associated with simultaneous events from the first real time processor to a second real time signal processor;

in the second real time signal processor transforming the actual location data received from the first real time signal processor to equivalent location data for a frame of reference in which a line connecting the two simultaneous events is at a preselected angle to the face of the detector when viewed in a transverse plane normal to the axis of the camera and calculating an equivalent detector angular position of the detector; and thereafter recording an event by incrementing a tally at a memory location corresponding to the equivalent location and detector angular position while collecting additional data.

2. The method of claim 1 including the step of applying a correction factor to the energy data based on the geometry of the detector.

3. The method of claim 2 including the step of comparing the corrected energy values to a range of acceptable values and rejecting the data if the corrected energy value is outside a selected range.

4. The method of claim 1 including the step of applying a linearity correction factor to energy data based on the geometry of the detector.

5. The method of claim 4 including the step of comparing the corrected energy data to a range of acceptable values and rejecting the data if the corrected energy value is outside a selected range.

6. The method of claim 5 including the steps of applying a correction factor to the energy data based on the geometry of the detector and thereafter rejecting the data if the corrected energy value is outside a selected range.

7. The method of claim 2 wherein the steps of applying a correction factor to the energy data is performed after said step of comparing the time of each event and before the step of transforming.

8. The method of claim 1 wherein the preselected angle is approximately 90°.

9. The method of claim 1, further including calculating and recording as the equivalent angle of incidence the angle between the line connecting two simultaneous events and the face of the detector measured in a plane which is perpendicular to the transverse plane and which includes the axis of the camera.

10. The method of claim 1 including recording events at memory locations corresponding to selected ranges of equivalent angles of incidence.

11. The method of claim 1 wherein the step of recording an event includes the steps of recording a plurality of events and further including the step of selecting a first range of acceptance values for the equivalent angle incidence and a second range of acceptance values for the equivalent angle of incidence and recording each event at a first memory location associated with the first range of acceptance values if the equivalent angle of incidence of the event is within the first range of acceptance values and simultaneously recording the event at a second memory location associated with the second range of acceptance values if the equivalent angle of incidence of the event is within the second range of acceptance values.

12. The method of claim 1 including selecting acceptance ranges for variables selected from the group including incident photon energy, transverse angle of incidence, and axial angle of incidence, and recording plural events each at a memory location associated with the selected ranges of values.

13. The method of claim 12 wherein the step of selecting values includes the step of selecting at least two ranges of acceptance values for at least one of the variables and recording events at memory locations associated with the selected ranges of values.

* * * * *